(12) United States Patent
Cui et al.

(10) Patent No.: US 10,391,111 B2
(45) Date of Patent: Aug. 27, 2019

(54) COMPOSITION FOR PREVENTING OR TREATING CERVICAL CANCER INCLUDING GYPENOSIDE LXXV

(71) Applicant: INTELLIGENT SYNTHETIC BIOLOGY CENTER, Daejeon (KR)

(72) Inventors: Chang Hao Cui, Daejeon (KR); Wan Taek Im, Daejeon (KR); Sun Chang Kim, Daejeon (KR)

(73) Assignee: Intelligent Synthetic Biology Center, Dajeon (KR)

( * ) Notice: Subject to any disclaimer, the term of this patent is extended or adjusted under 35 U.S.C. 154(b) by 0 days.

(21) Appl. No.: 15/512,026

(22) PCT Filed: Jun. 21, 2016

(86) PCT No.: PCT/KR2016/006565
§ 371 (c)(1),
(2) Date: Mar. 16, 2017

(87) PCT Pub. No.: WO2017/026641
PCT Pub. Date: Feb. 16, 2017

(65) Prior Publication Data
US 2018/0140623 A1 May 24, 2018

(30) Foreign Application Priority Data

Aug. 10, 2015 (KR) .................. 10-2015-0112613

(51) Int. Cl.
*A61K 31/704* (2006.01)
*A61P 35/00* (2006.01)
*A23L 33/10* (2016.01)

(52) U.S. Cl.
CPC ............ *A61K 31/704* (2013.01); *A23L 33/10* (2016.08); *A61P 35/00* (2018.01); *A23V 2002/00* (2013.01); *A23V 2200/308* (2013.01)

(58) Field of Classification Search
CPC .............................. A61K 31/704; A61P 35/00
See application file for complete search history.

(56) References Cited

U.S. PATENT DOCUMENTS

2014/0135278 A1* 5/2014 Liu .................... C07J 17/005
514/26

FOREIGN PATENT DOCUMENTS

| KR | 10-2008-0085292 | 9/2008 |
| KR | 10-2011-0067807 | 6/2011 |
| KR | 10-2012-0005896 | 1/2012 |
| KR | 10-2013-0069430 | 6/2013 |

OTHER PUBLICATIONS

An, Dong-Shan, et al. "Identification and characterization of a novel *Terrabacter ginsenosidimutans* sp. nov. β-glucosidase that transforms ginsenoside Rb1 into the rare gypenosides XVII and LXXV." *Applied and environmental microbiology* 76.17 (2010): 5827-5836.
Cui, C. et al., "Enhanced production of Gypenoside LXXV using a Novel Ginsenoside-transforming β-glucosidase from *Microbacterium* sp. Gsoil 167 and Anti-cancer activity", KMB 2015 42$^{nd}$ Annual Meeting, dated Jun. 24, 2015.
Gao, F. et al., "Biotransformation, a promising technology for anti-cancer drug development", Asian Pacific Journal of Cancer Prevention, 14(10), 5599-5608, 2013.
Hong, Hao, et al. "Enzymatic biotransformation of ginsenoside Rb1 and gypenoside XVII into ginesosides Rd and F2 by recombinant β-glucosidase from Flavobacterium Johnsoniae." *Journal of ginseng research* 36.4 (2012): 418-424.
Hou, J. G. et al., "Highly selective microbial transformation of major ginsenoside Rb1 to gypenoside LXXV by Esteya vermicola CNU120806", Journal of Applied Microbiology, 113(4), 807-814, 2012.
Lu, K. W. et al., "Gypenosides inhibited invasion and migration of human tongue cancer SCC4 cells through down-regulation of NF κ B and matrix metalloproteinase-9", Anticancer Research, 28(2A), 1093-1099, 2008.
Extended European Search Report issued in European Patent Application No. 16835283.9, dated Jan. 9, 2018.
Gao et al., "The anti-proliferation effect of gypenosides on cervical cancer HeLa cells and its molecular mechanism," *Tumor* 33.10 (2013): 868-872, (English Abstract).
Office Action issued in Japanese Patent Application No. 2017-514487 dated Dec. 12, 2017.
Korean Society for Microbiology and Biotechnology 2015 42nd Annual Meeting & International Symposium, Jun. 2015, E-43.

* cited by examiner

*Primary Examiner* — Jonathan S Lau
(74) *Attorney, Agent, or Firm* — Parker Highlander PLLC

(57) ABSTRACT

Provided are a pharmaceutical composition for preventing or treating cervical cancer including gypenoside LXXV or a pharmaceutically acceptable salt thereof as an active ingredient, a method of preventing or treating cervical cancer including administering the pharmaceutical composition to a subject excluding humans, a health functional food composition for preventing or improving cervical cancer including gypenoside LXXV as an active ingredient, and a feed composition for preventing or improving cervical cancer including gypenoside LXXV as an active ingredient.

5 Claims, 2 Drawing Sheets

COMPOSITION FOR PREVENTING OR TREATING CERVICAL CANCER INCLUDING GYPENOSIDE LXXV

This application is a national phase application under 35 U.S.C. § 371 of International Application No. PCT/KR2016/006565, filed Jun. 21, 2016, which claims priority to Korean Application No. 10-2015-0112613, filed Aug. 10, 2015, which are incorporated herein in their entirety.

BACKGROUND OF THE INVENTION

1. Field of the Invention

The present invention relates to a pharmaceutical composition for preventing or treating cervical cancer including gypenoside LXXV or a pharmaceutically acceptable salt thereof as an active ingredient, a method of preventing or treating cervical cancer including administering the pharmaceutical composition to a subject excluding humans, a health functional food composition for preventing or improving cervical cancer including gypenoside LXXV as an active ingredient, and a feed composition for preventing or improving cervical cancer including gypenoside LXXV as an active ingredient.

2. Description of the Related Art

Gypenoside (Gyp) is a triterpenoid saponin mainly included in *Gynostemma pentaphyllum*, and known to have a structure and a physiological activity very similar to those of ginsenoside. Until now, there have been about 100) kinds of gypenosides including gypenoside LXXV and gypenoside XVII.

Many efforts have been made to reveal the pharmacological use of gypenoside. Skin-whitening or hair growth-promoting effects of gypenoside isolated from a *Gynostemma pentaphyllum* Makino extract (Korean Patent Publication No. 10-2008-0085292), therapeutic or prophylactic effects of gypenoside isolated from a *Gynostemma pentaphyllum* extract on type 2 diabetes, obesity, or hyperlipidemia (Korean Patent Publication No. 10-2013-0069430), therapeutic or prophylactic effects of gypenoside on colitis (Korean Patent Publication No. 10-2012-0005896), etc. has been known, but the pharmacological effect of gypenoside on cervical cancer has not been clarified yet.

On the other hand, cervical cancer is the second leading cause of cancer deaths in women worldwide. The World Health Organization estimated that about 510,000 new cases of cervical cancer were diagnosed yearly and about 280,000 deaths accounting for about 56% of the cases occurred. About 90% or more of uterine cancer patients are cervical cancer patients, and cervical cancer is the most frequent malignant tumor with the highest incidence and mortality rate.

Under this background, the present inventors have made many efforts to demonstrate new pharmacological activities of gypenoside LXXV, and as a result, they found that gypenoside LXXV exhibits prophylactic or therapeutic effects on cervical cancer, thereby completing the present invention.

SUMMARY OF THE INVENTION

An object of the present invention is to provide a pharmaceutical composition for preventing or treating cervical cancer, including gypenoside LXXV represented by Chemical Formula 1 or a pharmaceutically acceptable salt thereof as an active ingredient.

Another object of the present invention is to provide a method of preventing or treating cervical cancer, including administering the pharmaceutical composition to a subject excluding humans.

Still another object of the present invention is to provide a health functional food composition for preventing or improving cervical cancer, including gypenoside LXXV represented by Chemical Formula 1 or a pharmaceutically acceptable salt thereof as an active ingredient.

Still another object of the present invention is to provide a feed composition for preventing or improving cervical cancer, including gypenoside LXXV represented by Chemical Formula 1 or a pharmaceutically acceptable salt thereof as an active ingredient.

DETAILED DESCRIPTION OF THE PREFERRED EMBODIMENTS

Figure 1:
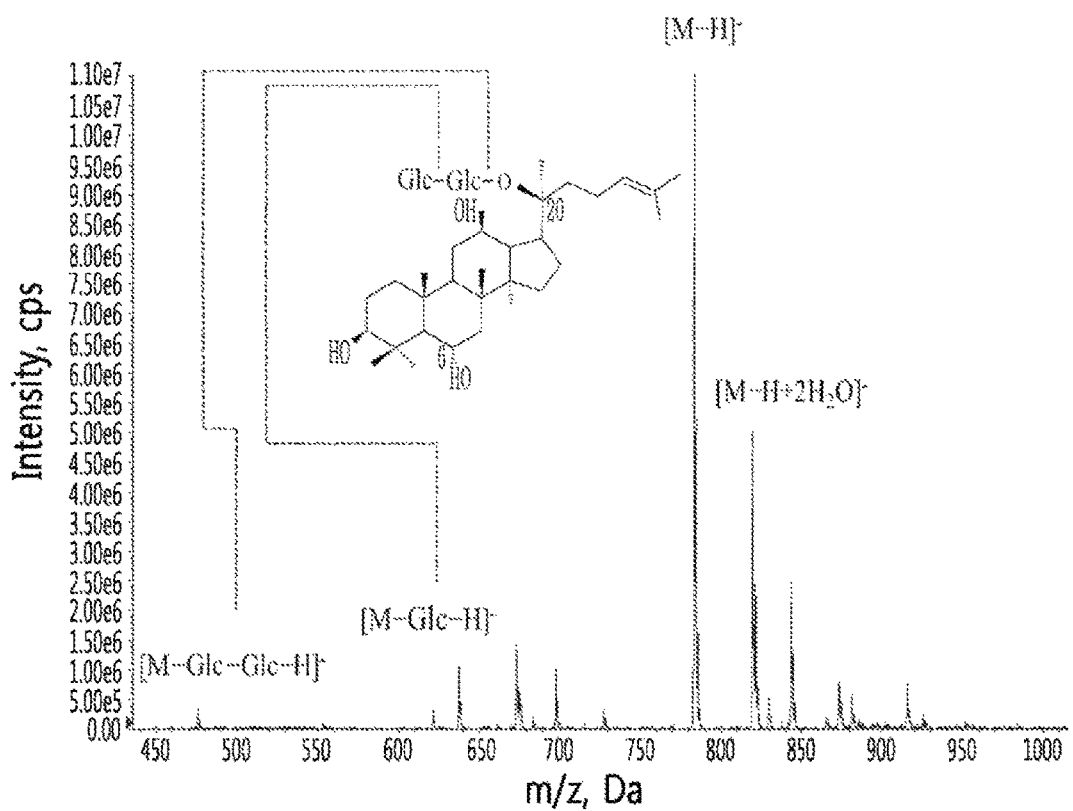
FIG. 1 is a chromatography showing HPLC result of gypenoside LXXV (GypLXXV) purified by Prep-HPLC, Glc representing a glucose moiety.

In one aspect to achieve the above objects, the present invention provides a pharmaceutical composition for preventing or treating cervical cancer, including gypenoside LXXV represented by Chemical Formula 1 or a pharmaceutically acceptable salt thereof as an active ingredient.

The term "gypenoside LXXV (GypLXXV)", as used herein, refers to a kind of gypenoside (Gyp), and has a chemical structure represented by the following Chemical Formula 1. The therapeutic effect of GypLXXV on cervical cancer has not been known until now, and first demonstrated by the present inventor.

[Chemical Formula 1]

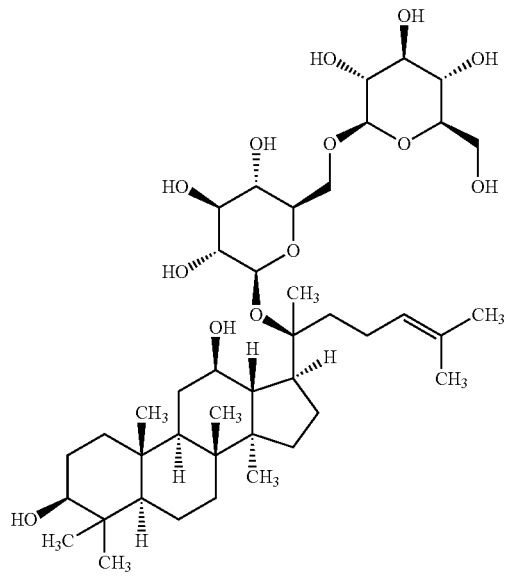

The term "gypenoside (Gyp)", as used herein, refers to triterpenoid saponin. The gypenoside includes GypXVII, GypXLIX, GypLXXIV, GypXLV, gypenoside UL1, gypenoside UL2, gypenoside UL3, gypenoside UL4, gypenoside UL5, gypenoside UL6, gypenoside UL7, etc., in addition to GypLXXV.

Gypenoside LXXV of the present invention may be obtained from ginsenoside Rb1 by deglycosylation according to a known method, or a commercially available gypenoside LXXV may be used.

The term "deglycosylation (deglycosylated)", as used herein, means elimination of glycoside from a glycoside-bound compound. The term "glycoside" refers to a molecule in which a sugar is bound to another functional group via a glycosidic bond. With respect to the objects of the present invention, the deglycosylation means that a glycoside in a ginsenoside compound is eliminated by hydrolysis, and the glycoside may be interpreted to have the same meaning as a glucose moiety.

The term "pharmaceutically acceptable salt", as used herein, refers to a pharmaceutically usable salt among salts composed of cations and anions bound together by electrostatic attraction. Commonly, the pharmaceutically acceptable salt may include metal salts, salts with organic bases, salts with inorganic acids, salts with organic acids, salts with basic or acidic amino acids, etc. For example, metal salts may include alkali metal salts (sodium salt, potassium salt, etc.), alkaline earth metal salts (calcium salt, magnesium salt, barium salt, etc.), aluminum salt, etc.; salts with organic bases may include triethylamine, pyridine, picoline, 2,6-lutidine, ethanolamine, diethanolamine, triethanolamine, cyclohexylamine, dicyclohexylamine, N,N-dibenzyl ethylenediamine, etc.; salts with inorganic acids may include hydrochloric acid, hydrobromic acid, nitric acid, sulfuric acid, phosphoric acid, etc, salts with organic acids may include formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, etc.; salts with basic amino acids may include arginine, lysine, ornithine, etc; and salts with acidic amino acids may include aspartic acid, glutamic acid, etc.

Further, since the compound according to the present invention may have an asymmetric carbon center, it may exist as an R or S isomer, a racemic mixture, a mixture of diastereomers, and respective diastereomers. All types of these isomers and mixtures may be also included in the scope of the present invention.

The term "cervical cancer", as used herein, refers to a malignant tumor arising from the cervix connected to the vagina. Cervical cancer is the second most common cancer m women worldwide, and about 80% of cervical cancer is known to occur in developing countries such as Asia, South America. Africa, etc. In Korea, cervical cancer is the fourth most common cancer, and cervical cancer patients are 4,394 cases, accounting for about 9.5% of the annual average female cancer of 46,476 cases.

Figure 2:
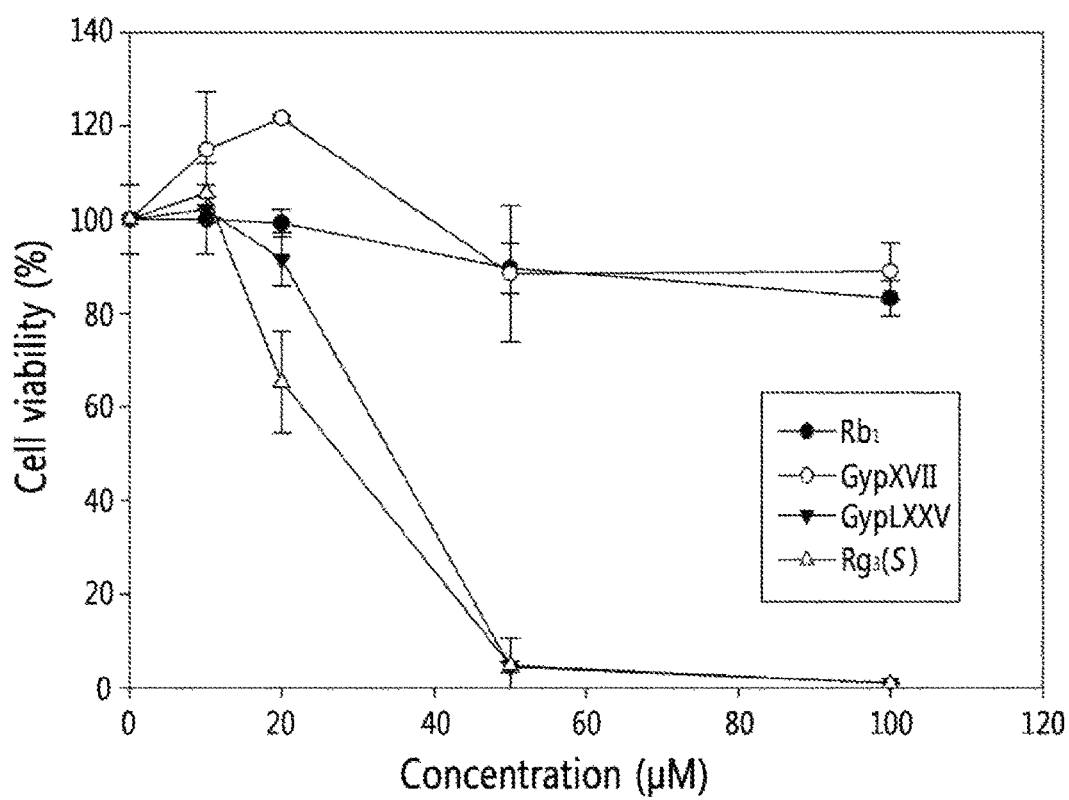
FIG. 2 is a graph showing anti-cancer effects of GypLXXV, Rg3(S), GypXVII, and Rb1 on HeLa cell viability, HeLa cells being incubated for 48 hrs in culture media with various concentrations of gypenoside and ginsenoside.

In an embodiment of the present invention, cytotoxic effect of GypLXXV represented by Chemical Formula 1 against cervical cancer HeLa cell was examined. It was confirmed that GypLXXV showed higher anti-cancer effects than Rb1 and GypXVII with more glucose moieties, and anti-cancer effects similar to commercially available Rg3(S) which has been applied to clinical trials (FIG. 2).

The term "preventing", as used herein, refers to all of the actions by which cervical cancer is restrained or retarded by administration of the pharmaceutical composition including GypLXXV of the present invention as an active ingredient.

The term "treating", as used herein, refers all of the actions by which symptoms of a subject suspected of having cervical cancer or having cervical cancer have taken a turn for the better or been beneficially changed by administration of the pharmaceutical composition.

The pharmaceutical composition of the present invention may include GypLXXV in an amount of 0.0001% by weight to 50% by weight, specifically, 0.01% by weight to 10% by weight, based on the total weight of the composition, but is not limited thereto.

The pharmaceutical composition of the present invention may further include a pharmaceutically acceptable carrier, excipient, or diluent which is commonly used in the preparation of pharmaceutical compositions. The carrier may include a non-naturally occurring carrier.

The term "pharmaceutically acceptable", as used herein, means a feature of being non-toxic to a cell or a human exposed to the composition.

Specifically, the pharmaceutical composition may be formulated in oral dosage forms, including powders, granules, tablets, capsules, suspensions, emulsions, syrup, aerosol, etc., preparations for external application, suppositories, and sterile injectable solutions. In the present invention, the carriers, excipients and diluents that may be included m the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate, and mineral oil. The pharmaceutical composition of the present invention may be formulated with commonly used diluents or excipients, such as fillers, extenders, binders, wetting agents, disintegrants, surfactants, etc. Solid formulations for oral administration may include tablets, pills, powders, granules, capsules, etc., and such solid formulations may be prepared by mixing with at least one excipient, for example, starch, calcium carbonate, sucrose, lactose, gelatin, etc. In addition to simple excipients, lubricants such as magnesium stearate or talc may also be used. Liquid formulations for oral administration may include suspensions, solutions for internal use, emulsions, syrup, etc., and may include various excipients, for example, wetting agents, flavoring agents, aromatics, preservatives, etc., in addition to water and liquid paraffin, which are frequently used simple diluents. Formulations for parenteral administration may include sterilized aqueous solutions, non-aqueous solutions, suspensions, emulsions, lyophilized preparations, and suppositories. As non-aqueous solvents or suspending agents, propylene glycol, polyethylene glycol, plant oils such as olive oil, injectable esters such as ethyl oleate, etc. may be used. As the base of the suppositories, witepsol, Macrogol, Tween 61, cacao butter, laurin butter, glycerogelatin, etc may be used.

In another aspect to achieve the above objects, the present invention provides a method of preventing or treating cervical cancer, including administering the pharmaceutical composition of the present invention to a subject excluding humans.

The term "administration", as used herein, means introducing a predetermined material into a subject by any suitable method.

The term "subject", as used herein, means all animals of rats, mice, livestock, including humans, which have developed or are at risk of developing cervical cancer. A specific example may be a mammal including a human.

Specifically, the method of preventing or treating cervical cancer of the present invention may include administering to a subject excluding humans a pharmaceutically effective amount of the pharmaceutical composition for preventing or treating cervical cancer, the composition including gypenoside LXXV represented by Chemical Formula 1 or a pharmaceutically acceptable salt thereof as an active ingredient.

The term "pharmaceutically effective amount", as used herein, means an amount which is sufficient to treat diseases at a reasonable benefit/risk ratio applicable to any medical treatment and does not cause any adverse effect. The effective dosage level may be readily determined by those skilled in the art, depending on factors, including the patient's sex, age, body weight, and health conditions, the kind and severity of the disease, the activity of the drug, drug sensitivity, administration method, administration time, administration route, excretion rate, the duration of treatment, drugs used in combination or used concurrently, and other factors known in the medical field.

The composition of the present invention may be administered in a daily dosage of specifically 0.0001 to 100 mg/kg (body weight), and more specifically 0.001 to 100 mg/kg (body weight), based on the solid components. The recommended dose may be administered once per day or in several divided doses per day.

In the method of preventing or treating cervical cancer of the present invention, the administration route and administration mode of administering the composition are not particularly limited, and the method may be performed according to any administration route and administration mode as long as the composition reaches a desired site. Specifically, the composition may be administered via various routes including oral or parenteral routes. Non-limiting examples of the administration routes may include oral, rectal, topical, intravenous, intraperitoneal, intramuscular, intraarterial, transdermal, or intranasal route, or inhalation.

In still another aspect to achieve the above objects, the present invention provides a health functional food composition for preventing or improving cervical cancer, including the compound represented by Chemical Formula 1 or a pharmaceutically acceptable salt thereof as an active ingredient.

The term "improving", as used herein, means all of the actions by which the parameters associated with conditions under treatment, for example, the symptoms are at least lessened.

When the health functional food composition of the present invention is used as a food additive, the composition may be added as it is or in combination with other foods or food ingredients, and may be used appropriately according to general methods.

Specifically, the health functional food composition may be in any one form of meats, sausages, bread, chocolate, candies, snack, confectionery, pizza, ramen, gum, ice cream, soups, beverages, teas, functional water, drinks, alcoholic beverages, and multi-vitamin preparations.

Further, the health functional food composition may further include various nutrients, vitamins, minerals (electrolyte), flavoring agents such as synthetic flavoring agents and natural flavoring agents, coloring agents and improving agents (cheese, chocolate, etc.), pectic acid and salts thereof, alginic acid and salts thereof, organic acids, protective colloidal thickening agents, pH controlling agents, stabilizing agents, preservatives, glycerin alcohol, carbonizing agents as used in carbonated beverages, etc. Additionally, the health functional food composition may include fruit flesh for the preparation of natural fruit juices, fruit juice beverages, and vegetable juices. These components may be used alone or in a mixture of two or more thereof.

Further, the health functional food composition may further include a food additive, and whether or not the health functional food composition is suitable as a "food additive material" is determined based on a standard and criteria relating to a relevant item according to general rules disclosed in Korean Food Additives Codex and a general test method that have been approved by Korea Food & Drug Administration as long as other rules is not provided.

The items disclosed m such "Korean Food Additives Codex" may include, for example, a chemically synthetic composite, such as ketone, glycine, calcium citrate, nicotinic acid, cinnamic acid, etc.; a natural additive material, such as persimmon color, a licorice extract, microcrystalline cellulose, Kaoliang color, guar gum, etc.; and mixed formulations, such as sodium L-glutamate formulation, alkali agents for noodles, preservative formulation, tar color formulation, etc.

In this regard, the content of gypenoside LXXV according to the present invention which is added to foods including beverages during preparation of health functional foods may be increased or decreased, if necessary. Specifically, gypenoside LXXV may be included in an amount of 0.01% by weight to 10% by weight, based on 100% by weight of the food, but is not limited thereto.

In still another aspect to achieve the above objects, the present invention provides a feed composition for preventing or improving cervical cancer, including the compound represented by Chemical Formula 1 or a pharmaceutically acceptable salt thereof as an active ingredient.

The term "feed", as used herein, refer to any natural or artificial diet, meal, etc., or components of such meal intended or suitable to be eaten, taken in, or digested by animals.

The feed may include a feed additive or an auxiliary feed.

A kind of the feed is not particularly limited, and any feed generally used in the art may be used. Non-limiting examples of the feed may include plant-based feeds, such as grams, nuts, food by-products, seaweeds, fibers, drug by-products, fats and oils, starches, meals, grain by-products, etc.; and animal-based feeds such as proteins, inorganic matters, fats and oils, minerals, single cell proteins, zooplanktons, foods, etc. These may be used alone or in a mixture of two or more thereof.

Hereinafter, the present invention will be described in detail with reference to the following Examples. However, these Examples are for illustrative purposes only, and the invention is not intended to be limited by these Examples.

Example 1.

Separation and Analysis of Gypenoside LXXV

Gypenoside LXXV (GypLXXV), gypenoside XVII (GypXVII), ginsenoside Rb1 (Rb1), and 20(S)-ginsenoside-Rg3 (Rg3(S)) were prepared according to a known method (Cui, C. H. et al., Appl Microbiol. Biotech., 2013, 97, 649-659.). To separate the above compounds, HPLC (High performance liquid chromatography) and LC/MSS analysis were performed.

HPLC analysis was performed using an HPLC system (Younglin Co. Ltd, Korea) with a quaternary pump, an automatic injector, and a single wavelength UV detector (model 730D), and Younglin's AutoChro 3000 software for peak identification and integration. The separation of ginsenoside was carried out on a Prodigy ODS(2) C18 column (5 μm, 150×4.6 mm i.d.; Phenomenex, USA) with a guard column (Eclipse XDB C18, 5 μm, 12.5×4.6 mm i.d.). The mobile phases were an acetonitrile solvent A and a distilled water solvent B. Gradient elution started with 32% solvent A and 68% solvent B, and was then changed as follows: A from 32% to 65%, 0-8 min, A from 65% to 100%, 8-12 min. A 100%, 12-15 min. A from 100% to 32%, 15-15.1 min, and A 32%, 15.1-25 min. An injection volume was 25 μL.

Thereafter, mass spectrometry of separated GypLXXV was performed by LC/MS/MS analysis, and a structure thereof was identified. A purification process was performed using a triple-quadrupole tandem mass spectrometer (API-2000, Applied Biosystems, Foster City. USA) in a negative ion mode, and then electrospray ionization mass spectrum (ESI-MS) of GypLXXV was measured. ESI parameters used were as follows: ionspray voltage, 24,200 V; ion source gas 1 (GS1), 20; curtain gas(CUR), 20; collision gas(CAD), 2. The declustering potential (DP), focusing potential (FP), entrance potential (EP), collision cell exit potential (CXP) and collision energy (CE) were variant with regard to measured ginsenosides. For MS analysis, the spectra were recorded in the m/z range from 400 to 1.000.

As a result, it was confirmed that electrospray ionization mass spectrum of the produced GypLXXV was 783.8 [M2H]$_2$ (FIG. 1).

Example 2.

Cytotoxic Effects of Gypenoside LXXV on HeLa Cells

To demonstrate cytotoxic effect of GypLXXV on tumor cells, a cervical cancer cell line, HeLa was used to compare cytotoxic effects of Rb1, GypXVII, Rg3(S) and GypLXXV on cell viability.

HeLa cells were cultured in DMEM (Dulbecco's Modified Eagle's Medium) containing 10% FBS, 2 mmol/L of glutamine, 100 U/mL penicillin, and 100 mg/mL of streptomycin at 37° C. under 5% $CO_2$ condition. An appropriate amount of GypLXXV in DMSO (dimethyl sulfoxide) was taken according to a final concentration as described and added to the culture medium.

In vitro chemosensitivity was measured by MTT (dimethyl thiazolyl-2,5-diphenyltetrazolium bromide) assay (CellTiter 96® Non-Radioactive Cell Proliferation Assay kit. Promega), 100 μl of HeLa cells were dispensed at a density of $10^4$ cells per well in a 96-well plate, and incubated for 24 hrs. To measure anti-proliferative effects of GypLXXV. Rg3(S). Rb1 and GypXVII, 2.5 μM to 100 μM of the compound was diluted with a FBS-free medium, and added to each well. Thereafter, the cells treated with the compound were incubated at 37° C. for 48 hrs, and MTT was added to each well, followed by further incubation for 4 hrs. After aspiration of the culture medium, formazan formed from MTT was dissolved in 100 μl of solubilization/stop solution. Thereafter, optical density of each well was measured at a wavelength of 595 nm using a microplate reader. Results were expressed as $LC_{50}$ values analyzed using a GraphPad Prism 5 program.

As a result, it was confirmed that Rg3(S) and GpLXXV treatment decreased cell division in a dose-dependent manner, 48 hrs later, almost all HeLa cells were inhibited by 50 μM of GypLXXV and Rg3(S). As confirmed in FIG. 2. $LC_{50}$ values of Rg3(S) and GypLXXV against HeLa cells were 23.48 μM±2.54 μM and 29.95 μM±5.75 μM, respectively. Through the results confirmed by the present invention, anti-cancer effects of GypLXXV was first demonstrated, and this compound was confirmed to show an anti-proliferative activity similar to that of Rg3(S) which has strong anti-cancer effects in vitro and in vivo as disclosed in many literatures (Lee. J. Y. et al., Molecular cancer therap., 2013, 12, 274-85, and Poon, P. Y. et al., Drug Metabol. Dispo., 2012, 40, 120-129.) (FIG. 2).

Many studies have been conducted on anti-cancer effects of rare ginsenosides (F2, Rg3(S), Rh2(S), CK and PPD) produced from ginsenoside Rb1 by deglycosylation, and their strong activities against various cancer cells were confirmed through many literatures (Lee. J Y. et al., Molecular cancer therap., 2013, 12, 274-85, and Cao, B. et al., Int. J. Cancer, 2013, 132, 1277-1287.). However, anti-cancer effects of GypLXXV were first revealed in the present invention, and GypLXXV was confirmed to show anti-cancer effects similar to those of commercially available Rg3(S) applied to clinical trials. Furthermore, GypLXXV was confirmed to show higher anti-cancer effects than those of Rb1 or GypXVII with more glucose moieties (FIG. 2).

Consequently, it was confirmed that GypLXXV has a therapeutic effect on cervical cancer in a dose-dependent manner.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

EFFECT OF THE INVENTION

Gypenoside LXXV of the present invention may be safely and effectively applied to the prevention and treatment of cancer.

What is claimed is:

1. A method for preventing or treating cervical cancer, comprising a step of administering a pharmaceutical composition comprising gypenoside LXXV represented by the following Chemical Formula 1 or a pharmaceutically acceptable salt thereof as an active ingredient:

[Chemical Formula 1]

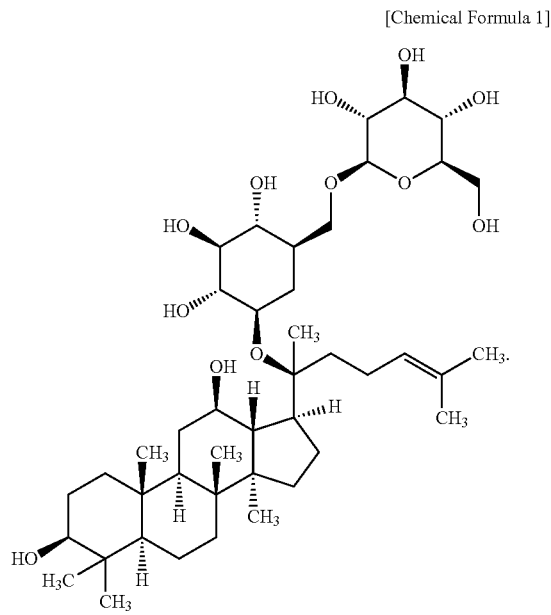

2. The method of claim 1, wherein the gypenoside LXXV is obtained from ginsenoside Rb1 by deglycosylation.

3. The method of claim 1, wherein the composition further comprises a pharmaceutically acceptable carrier, excipient, or diluent.

4. A method for improving cervical cancer, comprising a step of administering a pharmaceutically effective amount of gypenoside LXXV represented by the following Chemical Formula 1 or a pharmaceutically acceptable salt thereof:

[Chemical Formula 1]
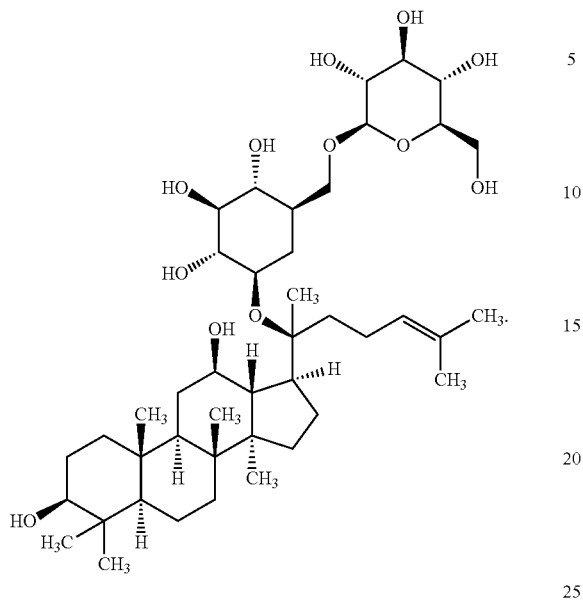
5. The method of claim 4, wherein the gypenoside LXXV is obtained from ginsenoside Rb1 by deglycosylation.
* * * * *

UNITED STATES PATENT AND TRADEMARK OFFICE
CERTIFICATE OF CORRECTION

PATENT NO. : 10,391,111 B2
APPLICATION NO. : 15/512026
DATED : August 27, 2019
INVENTOR(S) : Cui et al.

Page 1 of 2

It is certified that error appears in the above-identified patent and that said Letters Patent is hereby corrected as shown below:

In the Claims

In Claim 1, Column 8, Lines 36-57, delete the chemical formula and insert:

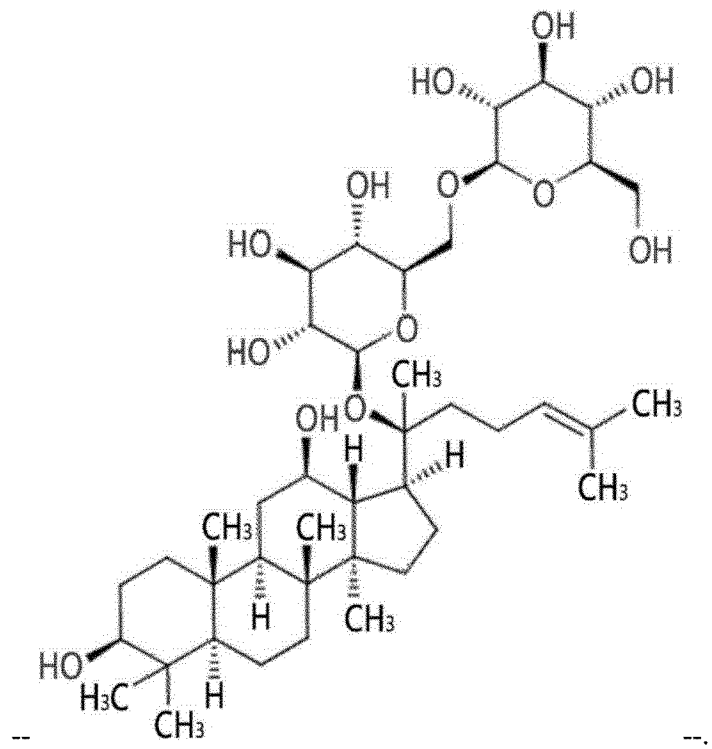

Signed and Sealed this
Twenty-ninth Day of October, 2019

Andrei Iancu
*Director of the United States Patent and Trademark Office*

CERTIFICATE OF CORRECTION (continued)
U.S. Pat. No. 10,391,111 B2

In Claim 4, Column 9, Lines 3-24, delete the chemical formula and insert:

-- 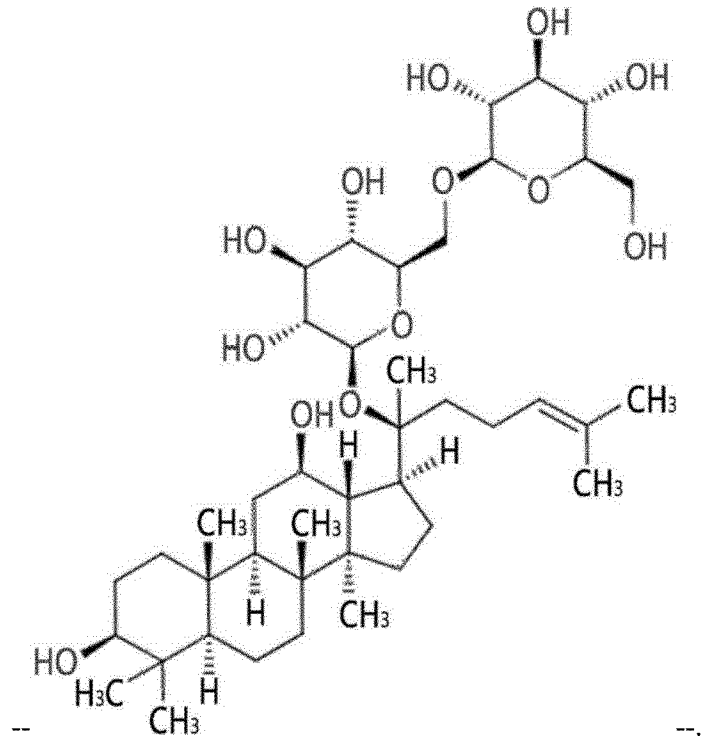 --.